United States Patent [19]

Kelly

[11] Patent Number: 5,698,760
[45] Date of Patent: Dec. 16, 1997

[54] OLEFIN METATHESIS

[75] Inventor: James Kelly, Stirling, Scotland

[73] Assignee: BP Chemicals Limited, England

[21] Appl. No.: 467,080

[22] Filed: Jun. 6, 1995

[30] Foreign Application Priority Data

Jul. 8, 1994 [GB] United Kingdom .................. 9413783

[51] Int. Cl.$^6$ ........................................ C07C 6/00
[52] U.S. Cl. ..................... 585/643; 585/644; 585/324
[58] Field of Search .............................. 585/644, 643, 585/324

[56] References Cited

U.S. PATENT DOCUMENTS 3,696,163  10/1972  Banks ........................................ 585/316
3,767,565  10/1973  Banks ........................................ 208/93

*Primary Examiner*—Walter D. Griffin
*Assistant Examiner*—In Suk Bullock
*Attorney, Agent, or Firm*—Brooks Haidt Haffner & Delahunty

[57] ABSTRACT

The present invention is a process for the production of a mixed C4 olefinic stream comprising primarily isobutene and butene-1, and propylene, said process comprising subjecting a mixed olefin feedstock comprising C5 olefins and ethylene to metathesis in the presence of a catalyst at a temperature in the range from about −20° C. to 200° C. and subjecting the resulting metathesis product to fractionation to recover the mixed C4 stream and propylene resulting therefrom. The production of MTBE or tertiary butyl alcohol or iso-butene sulphate from this C4 stream gives rise to substantially pure butene-1 as a by-product. This method therefore obviates the need separate butene-1 from butene-2 and conventional C4 saturated hydrocarbons as would be the case if a conventional MTBE raffinate had to be processed.

14 Claims, No Drawings

OLEFIN METATHESIS

The present invention relates to a process for the production of a mixture of butenes and propylene by metathesis of a feedstock comprising C5 olefins and ethylene.

It is well known that one of the by-products during the production of ethylene by steam cracking of liquid feedstock is a stream comprising C5 hydrocarbons which is known as "raw gasoline". This raw gasoline stream is conventionally subjected to hydrogenation to remove some of the dienes therein followed by distillation for separation into light and heavy gasoline streams. The lighter fraction is then further distilled to produce a C5 rich stream, the so-called "C5 light gasoline". Such a C5 light gasoline has a low octane number and is usually combined with a heavy gasoline stream to be added to conventional gasoline pools. Fluid catalytic cracking is another example of a process that produces a stream comprising C5 hydrocarbons.

It is also well known that due to environmental considerations, there is a serious demand for reduction in aromatic content and for minimising or eliminating lead additives of such gasoline. The reduction of these components in gasoline results in a significant loss of octane rating of the gasoline. Hitherto, this problem has been solved by incorporation of oxygenated compounds such as methyl tertiary butyl ether (MTBE) or ethyl tertiary butyl ether (ETBE) to the gasoline pool as high octane components. These components have excellent blending and vapour pressure characteristics and hence there is a great demand for such oxygenated compounds.

MTBE is produced by reacting isobutylene with methanol. Huge increases in the production of these raw materials have been observed and further accelerated growth is predicted. There are unlikely to be any problems with the production of methanol since the raw material which is natural gas is in plentiful supply and is relatively inexpensive. However, it is well recognised that the limiting step in the production of the aforementioned oxygenated compounds is the availability of isobutene.

Hitherto, isobutene has been produced by various routes including:

a. Catalytic dehydrogenation of isobutane: the disadvantage of this process is the very high capital cost of the plant.

b. Extraction of steam cracked C4 streams where the isobutene content thereof is first converted to MTBE and then back-cracked to substantially pure isobutene: this has the disadvantage that the main objective of the steam cracker is to produce ethylene and increasing the steam cracking temperature to maximise ethylene production will naturally reduce the isobutene content of the cracked gas.

c. Fluid catalytic cracking (FCC): this has the disadvantage that the main function of an FCC unit is the production of transport fuels whilst minimising the formation of light ends; any light ends formed are converted to gasoline by alkylation.

d. Isomerisation of butene-1: this has the disadvantage that butene-1 itself is produced either
  i. by fractionation of a raffinate resulting from the conversion of isobutene in a mixed C4 stream to MTBE, or,
  ii. by extractive distillation of mixed butene streams, or
  iii. by dimerisation of ethylene.

Of these, (i) is the most commercially viable and most economic.

Butenes have also been produced by the disproportionation of olefins especially pentenes, particularly pentene-1 and pentene-2, and hexenes. In most cases these olefins are disproportionated on their own or in conjunction with other lower olefins such as propylene. Examples of prior publications describing such reactions include U.S. Pat. Nos. 4,331,559, 4,291,187, 4,269,780, 4,071,471, 4,262,156, 3,761,537, 4,922,048, 5,191,144, 5,264,635, and J-A-48031194. None of these or other prior art references in this field disclose the metathesis of a feedstock comprising a mixture of C5 olefins and ethylene.

It has now been found that the C5 light gasolines referred to above can be a valuable source of both isobutene and n-butenes which thereby not only enhances the value derivable from the light gasoline stream but is also a source of these C4 olefins and produces, in addition, propylene as by-product.

Accordingly, the present invention is a process for the production of a mixed C4 olefinic stream comprising primarily isobutene and butene-1, and propylene, said process comprising subjecting a mixed olefin feedstock comprising C5 olefins and ethylene to metathesis in the presence of a catalyst at a temperature in the range from about −20 C. to 200° C. and subjecting the resulting metathesis product to fractionation to recover the mixed C4 stream and propylene resulting therefrom.

The feedstock for this reaction comprises C5 olefins and ethylene. The C5 olefins in the feedstock suitably comprise one or more of pentene-1, pentene-2, 2-methylbutene-2, 2-methylbutene-1 and 3-methylbutene-1. Such a feedstock may be obtained from a by-product during the steam cracking of naphtha to ethylene. This by-product usually comprises significant amounts of isomeric C5 paraffins, pentadienes, pentenes and small amounts of isomeric hexanes. When this by-product is subjected to a selective hydrogenation step followed by fractionation to remove C6 hydrocarbons, the resultant hydrogenated product comprises about 50% w/w of isomeric pentanes and about 47% w/w of isomeric pentenes but has virtually no pentene-1 or dienes. The selective hydrogenation step is suitably carried out in the presence of a conventional hydrogenation catalyst such as eg a nickel or palladium based catalyst. Two typical examples of such feedstock compositions from different refineries and the approximate concentration of the major components in such feedstocks are tabulated below:

TABLE 1

| Component | Refinery A (Wt %) | Refinery B (Wt %) |
|---|---|---|
| n/i-Pentane | 32 | 44 |
| Cyclopentane | 5 | 5.8 |
| Pentene-1 | 2 | 8.2 |
| Pentene-2 | 9 | 8.2 |
| 2-Methylbutene-1 | 3.6 | 5.6 |
| 2-Methylbutene-2 | 7.4 | 11.2 |
| 3-Methylbutene-1 | 0.5 | 1.3 |
| Cyclopentadiene | 9.1 | 7.4 |
| Linear dienes | 3 | 0.5 |
| C6s | 28.4 | 7.8 |

Taking a sample of an actual feedstock from Refinery A, the effect of deep hydrogenation followed by fractionation of the hydrogenated product to remove C6 hydrocarbons on the composition of the feedstock is shown in Table 2 below in which all units are % w/w of the total. As can be seen from Table 2, a feature of this hydrogenation step is that most, if not all, of the pentene-1 present in the original by-product is hydroisomerised to pentene-2 during this step. Furthermore, the original content of pentene-2 (8.43% w/w) and 2-methylbutene-2 (6.9% w/w) in the by-product is virtually doubled to 16.04% w/w and 17.1% w/w respectively in the hydrogenated product after the removal of the C6 components.

TABLE 2

| Component | Untreated | Post Deep Hydrogenation | Post C6 Removal |
|---|---|---|---|
| n-Pentane | 19.49 | 19.49 | 25.62 |
| iso-Pentane | 13.64 | 13.64 | 17.93 |
| Cyclopentane | 4.35 | 6.17 | 8.11 |
| Pentene-1 | 1.99 | 0 | 0 |
| 2-methylbutene-1 | 3.68 | 0 | 0 |
| 3-methylbutene-1 | 0.53 | 0 | 0 |
| cis-Pentene-2 | 2.1 | 3.99 | 5.25 |
| trans-Pentene-2 | 6.33 | 8.22 | 10.81 |
| 2-methylbutene-2 | 6.9 | 11.11 | 17.1 |
| Cyclopentene | 9.09 | 10.91 | 14.34 |
| 1-cis-3-Pentadiene | 0.56 | 0 | 0 |
| 1-trans-3-Pentadiene | 0.84 | 0 | 0 |
| 1,4-Pentadiene | 0.38 | 0 | 0 |
| Isoprene | 1.89 | 0 | 0 |
| Cyclopentadiene | 3.64 | 0 | 0 |
| n-Hexane | 5.74 | 5.74 | 0 |
| 2-Methylpentane | 5.44 | 5.44 | 0 |
| 3-Methylpentane | 2.32 | 2.32 | 0 |
| 2,3-Dimethylbutane | 0.32 | 0.32 | 0 |
| Cyclohexane | 0 | 0 | 0 |
| Methylcyclopentane | 1.19 | 1.19 | 0 |
| Benzene | 1.06 | 1.06 | 0 |
| Other C6's | 7.65 | 7.65 | 0 |
| Toluene | 0.02 | 0.02 | 0 |

The ratio of the ethylene to C5 olefins in the mixed olefinic feedstock subjected to metathesis is suitably in the range from about 1:1 to about 10:1, preferably from about 1:3 to about 1:6, eg about 1:4 w/w. The use of excess ethylene suppresses the self metathesis of the C5 olefins.

The metathesis reaction is carried out in the presence of a catalyst. Examples of catalysts that may be used include a supported metal oxide such as an oxide of rhenium, tungsten, molybdenum or cobalt. The support may be alumina, silica, molybdena, zirconia or yttria. These supports may be dosed with other compounds capable of promoting the reaction such as eg phosphorus compounds, eg phosphates; tin compounds such as (alkyl)tin halides; and alkali and alkaline earth metals such as eg sodium, potassium and calcium. Supports such as alumina may be used in their various allotropic forms such as eg γ-alumina. The preferred catalyst is suitably rhenium heptoxide on alumina which may be phosphated alumina. The amount of metal oxide with respect to the support in the catalyst is suitably in the range from about 0.1 to about 15 % w/w, preferably from 0.1 to about 10% w/w, more preferably from about 0.5% to about 5% w/w. The process can advantantageously use a metathesis catalyst comprising rhenium heptoxide on alumina (8% wt rhenium metal), prepared according to the teaching of U.S. Pat. No. 4,795,734.

The metathesis reaction is suitably carried out under heterogeneous conditions. A solvent may be used as the reaction medium to keep the reactants and products in a liquid form, if this is desirable, although this may not be necessary where the reaction is carried out under pressure. A diluent which is inert under the reaction conditions may also be used, if desired. Examples of such diluents may be paraffinic or cycloparaffinic hydrocarbons.

The reaction is suitably operated under pressure so that the reactants and products are maintained in the liquid phase at the reaction temperature and under the reaction conditions. Thus, the pressures used may suitably range from about 100 to about 10000 kPa, preferably from about 100 to about 5000 kPa.

The metathesis reaction is suitably carried out at a temperature in the range from about −20° C. to about 200° C., preferably from about 0° C. to about 150° C. and more preferably from about 15° C. to about 40° C.

The reaction is not dependent upon the cis- or trans-configuration of the olefins and thus all pentene-2 present in the feed is available for the reaction.

The reaction is suitably carried out at a liquid hourly space velocity (LHSV) in the range from about 1 to about 30/hr by volume. The reaction may be typically represented by the following equation:

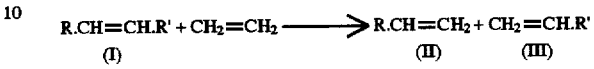

wherein R and R' represent various alkyl groups which, when taken together with the .CH=CH. functions in (I) above, represent isomeric C5 olefins. The products (II) and (III) shown above are two of the major products that are formed in the reaction. Typically, metathesis of pentene-2 and ethylene would give rise to a mixture of propylene and butene-1 whereas metathesis of 2-methylbutene-2 and ethylene would give rise to isobutene and propylene. Thus, the products of the metathesis reaction are a mixture of isobutene, butene-1 and propylene.

The products of the reaction can be fractionated to recover propylene on the one hand and a substantially pure mixture of isobutene and butene-1 on the other hand. The first distilate from the reaction mixture is of propylene and unreacted ethylene. The bottoms from this distillation step comprise a mixture of isobutene, butene-1 and unreacted C5 hydrocarbons. The bottoms may be fed to a second distillation stage where a mixture of isobutene and butene-1 are recovered overhead. The base products from this second distillation stage comprising unreacted C5 hydrocarbons is usually highly paraffinic and can therefore be used as a valuable steam cracker feed. The mixture of isobutene and butene-1 is difficult to separate by simple fractionation due to the close proximity of their boiling points (−6.9° C. versus −6.3° C.). This mixture may, however, be separated by reaction eg with an alcohol such as methanol or ethanol so that the isobutene is converted to the corresponding ether MTBE or ETBE leaving behind a substantially pure form of butene-1. The ether may be back-cracked to recover pure isobutene. Alternatively, butene-1 can be separated by absorption techniques. Pure butene-1 is a valuable feedstock for producing a number of compounds including inter alia polybutene-1.

The spent or deactivated catalyst from the reaction can by regenerated by thermal oxidation ie by heating at elevated temperatures above 300° C. in the presence of oxygen or a gas containing oxygen.

A feature of this process is that the metathesis followed by fractional distillation produces a C4 stream containing only isobutene and butene-1. The production of MTBE or tertiary butyl alcohol or iso-butene sulphate from this C4 stream gives rise to substantially pure butene-1 as a by-product. This method therefore obviates the need separate butene-1 from butene-2 and conventional C4 saturated hydrocarbons as would be the case if a conventional MTBE raffinate had to be processed. Furthermore, the metathesis product of a feed comprising C5 olefins and ethylene is substantially free of undesirable butene-2, which is invariably present when ethylene in the feed is substituted by propylene.

The present invention is further illustrated with reference to the following Examples.

Example 1

This Example illustrates the invention through conversion of a synthetic liquid feedstock containing 9.05% wt. of 2-methylbutene-2 in cyclohexane diluent with ethylene to produce iso-butene and propylene over a typical heterogeneous metathesis catalyst comprising rhenium heptoxide on alumina (8% wt rhenium metal), prepared according to the teaching of U.S. Pat. No. 4,795,734.

The Example was carried out on a continuous basis using a fixed catalyst bed in a stainless steel reactor (32.5 mm internal diameter) located within an electric furnace. Reaction temperature was monitored using thermocouples located at the top and bottom of the catalyst bed. Metered gaseous and liquid reactants were fed upflow through the reactor. Gaseous and liquid products were separated on exit from the reactor and analysed using gas chromatography.

Process conditions

The metathesis catalyst (100 ml) was activated in situ in the reactor by heating for 12 hours at 550° C. under an air purge (atmosphere press, GHSV=500). After this oxidation stage, the reactor was purged at 550° C. with nitrogen (atmospheric pressure, GHSV=500) for 1 hour prior to cooling, under nitrogen, to the required start of run reaction temperature of 40° C.

The reactor was pressurised to the operating pressure of 30 barg with nitrogen prior to the introduction of the gaseous and liquid reactants. The nitrogen flow was replaced with ethylene, fed at the required rate for the reaction (44 liters/hr at NTP). The synthetic liquid feed was fed to the reactor at 150 ml/hr (LHSV=1.5/hr. The approximate mole ratio of ethylene to C5 hydrocarbons is in the region of 10:1. A reactor pressure of 30 barg was maintained for the duration of the experiment. The average catalyst bed temperature was increased to approximately 51° C. after 90 hrs on stream when 2-methylbutene-2 conversion had fallen to 50% of its start of the run value. The run was terminated after 128 hours on stream.

The results are shown in Table 3 below and are quoted on a mol % basis.

TABLE 3

2-Methylbutene-2 Metathesis with Ethylene

| TOS (hrs) | Av Bed Temp °C. | 2-MB-2 Conv. | iso-Butene Selec. | TOS (hrs) | Av Bed Temp °C. | 2-MB-2 Conv | iso-Butene Selec. |
|---|---|---|---|---|---|---|---|
| 18 | 41.2 | 81.3 | 71.83 | 70 | 40.1 | 47.45 | 94.27 |
| 19 | 41.1 | 79.26 | 74.31 | 73 | 40.2 | 47.70 | 91.31 |
| 20 | 40.9 | 83.77 | 73.62 | 76 | 40.1 | 46.59 | 87.32 |
| 21 | 41.1 | 77.62 | 74.31 | 79 | 39.9 | 47.14 | 93.33 |
| 22 | 41.1 | 74.09 | 74.16 | 82 | 39.9 | 47.31 | 93.99 |
| 24 | 41.1 | 71.93 | 77.98 | 88 | 39.9 | 37.77 | 99.37 |
| 26 | 41.1 | 69.91 | 82.81 | 91 | 48.3 | 37.82 | 85.71 |
| 28 | 41.1 | 78.22 | 82.62 | 93 | 50.9 | 59.45 | 84.89 |
| 30 | 41.2 | 73.44 | 93.35 | 95 | 51.5 | 60.71 | 86.88 |
| 32 | 41.1 | 72.18 | 82.83 | 97 | 51.3 | 52.76 | 91.54 |
| 39 | 40.4 | 65.15 | 86.11 | 99 | 51.3 | 48.86 | 85.17 |
| 41 | 40.8 | 71.77 | 87.75 | 101 | 51.3 | 47.22 | 89.41 |
| 43 | 40.8 | 67.28 | 82.2 | 103 | 51.6 | 46.62 | 93.19 |
| 45 | 40.7 | 56.82 | 89.56 | 105 | 51.3 | 36.37 | 98.21 |
| 47 | 40.6 | 64.83 | 88.81 | 109 | 51.4 | 40.63 | 92.64 |
| 49 | 40.6 | 62.23 | 91.81 | 111 | 51.5 | 37.97 | 96.04 |
| 52 | 40.5 | 60.01 | 85.87 | 116 | 51.5 | 29.15 | 92.32 |
| 55 | 40.5 | 59.79 | 92.31 | 119 | 51.8 | 31.16 | 89.82 |
| 58 | 40.4 | 54.98 | 94.64 | 122 | 51.9 | 26.19 | 100 |
| 61 | 40.4 | 52.14 | 96.33 | 125 | 52.1 | 26.11 | 100 |
| 67 | 40.3 | 49.81 | 82.99 | 128 | 52.9 | 28.06 | 98.98 |

These results show that isobutene was the only C4 olefin in the product. The reduction in selectivity was due to the formation of light polymer. These results demonstrate that the metathesis reaction between 2-methylbutene-2 and ethylene is very selective for the formation of isobutene as the only C4 olefin product.

Example 2

This Example illustrates the invention through the production of butene-1, iso-butene and propylene by reaction of a synthetic liquid feedstock containing by weight 3.1% trans-pentene-2, 1.2% cis-pentene-2 and 7.8% 2-methylbutene-2 in cyclohexane diluent, with ethylene over an olefin disproportionation catalyst. The catalyst used was supplied by Engelhard de Meern BV (Ref. Q195-01) and comprised typically 3% by weight of rhenium supported on 1.6 mm extrudates of alumina. The experiment was conducted on a continuous basis using a fixed catalyst bed in a stainless steel reactor (32.5 mm internal diameter) located within an electric furnace. Reaction temperature was monitored using thermocouples located at the top and bottom of the catalyst bed. Metered gas and liquid reactants were fed upflow through the reactor. Gas and liquid products were separated on exit from the reactor and analysed using gas chromatography.

The metathesis catalyst (100 ml) was actuated in situ in the reactor by heating for 12 hours at 550° C. under an air purge (atmospheric pressure, GHSV=500). After this oxidation stage the reactor was purged at 550° C. with nitrogen (atmospheric pressure, GHSV=500) for 1 hour prior to cooling, under nitrogen, to the required start of run reaction temperature of 40° C.

The reactor was pressurised to the operating pressure of 3000 kPa (30 barg) with nitrogen prior to the introduction of the gas and liquid reactants. The nitrogen flow was replaced with ethylene, fed at the required rate for the reaction (24 l/hr. at NTP). The synthetic liquid feed was fed to the reactor at 75 ml/hr. (LHSV=0.75/hr). A reactor pressure of 3000 kPa (30 barg) was maintained for the duration of the experiment. The reactor inlet (catalyst bed bottom) temperature was increased to approximately 51° C. after 27 hours-on-stream (HOS) when 2-methylbutene-2 conversion had fallen to less than 50% of its start of run value. The run was terminated after 42 HOS. The results are shown in Table 4 below:

TABLE 4

| HOS | 2-MB-2 CONV. | c-Pentene-2 Conversion | t-Pentene-2 Conversion | i-Butene Selectivity | 1-Butene Selectivity |
|---|---|---|---|---|---|
| 2 | 64 | 92 | 81 | 66 | 68 |
| 8 | 55 | 97 | 88 | 64 | 65 |
| 14 | 50 | 94 | 73 | 57 | 65 |
| 42 | 10 | 31 | 12 | 96 | 55 |

The above results show that the primary product of the metathesis is a C4 olefinic stream comprising iso-butene and butene-1 with a mole of propylene being formed for each mole of the C4 olefin.

We claim:

1. A process for making a mixed $C_4$ olefinic stream comprising primarily isobutene and butene-1, and propylene which comprises:

(i) steam cracking naptha to ethylene and recovering as a by-product a $C_5$ olefinic feedstock comprising significant amounts of isomeric $C_5$ paraffins, pentadienes, pentenes and small amounts of isomeric hexenes;

(ii) selectively hydrogenating said $C_5$ olefinic by-products in the presence of a hydrogenation catalyst followed by fractionation to remove $C_6$ hydrocarbons;

(iii) subjecting the selectively hydrogenated mixed $C_5$ olefinic feedstock from step (ii) and ethylene to metathesis in the presence of a catalyst and at a temperature of −20° C. to 200° C.; and (iv) fractionating the resulting metathesis product from step (iii) to recover the mixed $C_4$ stream and propylene resulting therefrom.

2. A process according to claim 1 wherein the C5 olefins in the feedstock comprise one or more of pentene-1, pentene-2, 2-methylbutene-2, cyclopentene, 2-methylbutene-1 and 3-methylbutene-1.

3. A process according to claim 1 wherein the ratio of the ethylene to C5 olefins in the mixed olefinic feedstock subjected to metathesis is in the range from about 1:1 to about 10:1 w/w.

4. A process according to claim 1 wherein the metathesis reaction is carried out in the presence of a catalyst comprising at least one supported metal oxide selected from the group consisting of an oxide of rhenium, tungsten, molybdenum and cobalt.

5. A process according to claim 4 wherein the support on which the metal oxide catalyst is supported is selected from the group consisting of at least one of alumina, silica, molybdena, zirconia and yttria.

6. A process according to claim 1 wherein the metathesis is carried out using a catalyst composition comprising rhenium heptoxide supported on alumina.

7. A process according to claim 6 wherein the alumina support used is γ-alumina.

8. A process according to claim 5 wherein said support is dosed with a promoter capable of promoting the reaction and is selected from the group consisting of phosphorous compounds, tin compounds, alkali metals and alkaline earth metals.

9. A process according to claim 5 wherein the amount of metal oxide with respect to the support in the metathesis catalyst is in the range from about 0.1 to about 15% w/w.

10. A process according to claim 1 wherein the metathesis reaction is carried out under heterogeneous conditions.

11. A process according to claim 1 wherein the metathesis reaction is operated under pressure so that the reactants and products are maintained in the liquid phase at the reaction temperature and under the reaction conditions.

12. A process according to claim 1 wherein the metathesis reaction is carried out at pressures in the range from about 100 to about 10000 kPa and at temperatures in the range from about $-20°$ C. to about $200°$ C.

13. A process according to claim 1 wherein the metathesis reaction is carried out at a liquid hourly space velocity (LHSV) in the range from about 1 to about 30 by volume per hour.

14. A process according to claim 1 wherein the mixed butenes formed by the metathesis reaction is substantially free of butene-2.

* * * * *

UNITED STATES PATENT AND TRADEMARK OFFICE
CERTIFICATE OF CORRECTION

PATENT NO.   :   5,698,760
DATED        :   December 16, 1997
INVENTOR(S)  :   JAMES KELLY It is certified that error appears in the above-identified patent and that said Letters Patent is hereby corrected as shown below:

Column 2, Table 1, first column, correct first entry under "Component" to read --n/i-Pentane--

Signed and Sealed this

Second Day of June, 1998

Attest:

BRUCE LEHMAN

*Attesting Officer*   *Commissioner of Patents and Trademarks*